United States Patent [19]

Bietti et al.

[11] Patent Number: 4,548,944
[45] Date of Patent: Oct. 22, 1985

[54] GUANIDINO-HETEROCYCLYL-PHENYL-AMIDINES AND SALTS THEREOF

[75] Inventors: Giuseppe Bietti, Milan; Enzo Cereda, Tortona; Arturo Donetti, Milan; Piero del Soldato, Monza; Antonio Giachetti; Rosamaria Micheletti, both of Milan, all of Italy

[73] Assignee: Istituto de Angeli S.p.A., Milan, Italy

[21] Appl. No.: 465,572

[22] Filed: Feb. 10, 1983

[30] Foreign Application Priority Data

Mar. 24, 1982 [IT] Italy ............................... 20356 A/82

[51] Int. Cl.⁴ .................. C07D 277/42; A61K 31/425
[52] U.S. Cl. .................................. 514/363; 514/369; 514/370; 514/377; 514/925; 548/133; 548/138; 548/193; 548/178; 548/233; 546/209; 544/133; 544/138; 544/139
[58] Field of Search ............... 548/133, 198, 138, 193, 548/233; 424/270, 269, 272; 544/133, 138, 139; 546/209

[56] References Cited

FOREIGN PATENT DOCUMENTS 3640 8/1979 European Pat. Off. ............ 548/198

Primary Examiner—Robert Gerstl
Attorney, Agent, or Firm—Hammond & Littell, Weissenberger & Dippert

[57] ABSTRACT

Compounds of the tautomeric formula

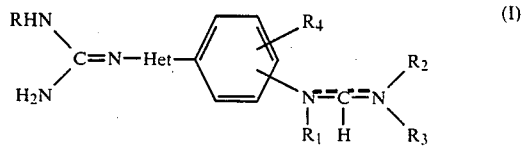

wherein
 R, $R_1$ and $R_2$, which may be identical to or different from each other, are each hydrogen or alkyl of 1 to 4 carbon atoms;
 $R_3$ is straight or branched alkyl, optionally interrupted by heteroatoms such as oxygen, sulfur or nitrogen; straight or branched alkenyl; alkynyl; cyano; cycloalkyl or cycloaliphatic alkyl; a bicyclic group; aryl; or a heterocyclic group; or
 $R_2$ and $R_3$, together with each other and the nitrogen atoms to which they are attached, form a heterocyclic group;
 $R_4$ is hydrogen, halogen, alkyl of 1 to 4 carbon atoms or alkoxy of 1 to 4 carbon atoms; and
 Het is a substituted or unsubstituted heterocycle containing two or three heteroatoms;

tautomers thereof, and non-toxic, pharmacologically acceptable acid addition salts thereof. The compounds as well as their salts are useful as anti-ulcerogenics.

20 Claims, No Drawings.

GUANIDINO-HETEROCYCLYL-PHENYL-AMIDINES AND SALTS THEREOF

This invention relates to novel guanidine-heterocyclyl-phenyl-amidines and acid addition salts thereof, to methods of preparing these compounds, to pharmaceutical compositions containing them as active ingredients, and to a method using them as anti-ulcerogenics.

BACKGROUND OF THE INVENTION AND THE PRIOR ART

Histamine antagonists have been studied for many years. In the last forty years, various substances, such as mepyramine, were found to antagonize certain effects ($H_1$) of histamine. These substances however had no effect on gastric acid secretion which is mediated by other histamine receptors ($H_2$) [Black et al.,-Nature 236, 385, (1972)]. With the advent of cimetidine, preceded by two other compounds (burimamide and metiamide), a new type of antihistamines ($H_2$-blockers) has been discovered which are capable of antagonizing those responses (for instance gastric acid secretion) which are unaffected by classical antihistamines ($H_1$-blockers). More recently, new $H_2$-receptor antagonists, that is, ranitidine [Bradshaw et al., Brit J. Pharmacol. 66, 464 P, (1979)], tiotidine [P.O. Jellin, Life Sci., 25, 2001, (1979)] and BL 6341 [Cavanagh et al., Fed. Proc., 40, 2652, (1981)], have been reported to be more potent than cimetidine, both as $H_2$-receptor antagonists "in vitro" and as inhibitors of gastric acid secretion "in vivo".

All of these compounds share a common feature, namely a methylthioethyl side-chain ($-CH_2SCH_2CH_2-$) bearing neutral polar groups connecting basic or basic-substituted heterocyclic rings.

In our Italian Patent Application Ser. No. 26323 A/80 we have described a new type of $H_2$-receptor antagonists, that is, imidazolyl-phenyl-amidines, which are potent $H_2$-receptor antagonists and inhibitors of gastric acid secretion. With respect to cimetidine, the imidazole ring is retained in these compounds, whereas the methylthioethyl side-chain is replaced by a phenyl ring connected to an amidino group.

DESCRIPTION OF THE INVENTION

More particularly, the present invention relates to a novel class of compounds represented by the formula

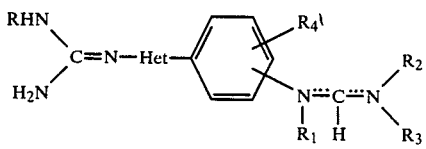

(I)

wherein
- R, $R_1$ and $R_2$, which may be identical to or different from each other, are each hydrogen or alkyl of 1 to 4 carbon atoms;
- $R_3$ is straight or branched alkyl, optionally interrupted by heteroatoms such as oxygen, sulfur or nitrogen; straight or branched alkenyl; alkynyl; cyano; cycloalkyl or cycloaliphatic alkyl; a bicyclic group; aryl; or a heterocyclic group; or '$R_2$ and $R_3$, together with each other and the nitrogen atom to which they are attached, form a heterocyclic group;
- $R_4$ is hydrogen, halogen, alkyl of 1 to 4 carbon atoms or alkoxy of 1 to 4 carbon atoms; and
- Het is a substituted or unsubstituted heterocycle containing two or three heteroatoms;

tautomers thereof, and non-toxic, pharmacologically acceptable acid addition salts thereof.

The dotted lines in the amidine moiety of formula I indicate two tautomeric forms, namely

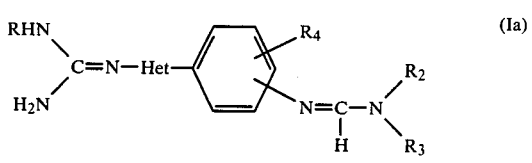

(Ia)

and

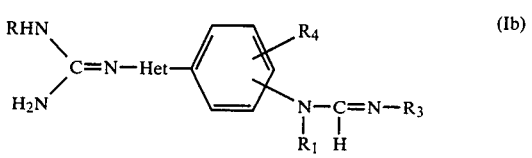

(Ib)

Although the double bonds in the other moieties have been shown in particular positions, other tautomeric forms are possible, and the present invention includes such tautomeric forms within its scope, both in terms of the compounds of the invention and in terms of the processes for their preparation.

When, in the compounds of the formula I, R, $R_1$ and/or $R_2$ are alkyl groups of 1 to 4 carbon atoms, these may, for example, be methyl or ethyl; in particular, with the proviso that when $R_1$ is present, $R_2$ is absent and vice-versa; when $R_3$ is a straight or branched alkyl group it may, for example, be an alkyl group containing from 1 to 8 carbon atoms which may optionally contain an oxygen atom, such as methoxyethyl or hydroxypropyl; a sulfur atom, such as methylthioethyl; or a nitrogen atom, such as cyanoethyl; when $R_3$ is a straight or branched alkenyl group it may, for example, be an alkenyl group containing from 3 to 5 carbon atoms; when $R_3$ represents the alkynyl group it may, for example, be an alkynyl group containing 3 or 4 carbon atoms; when $R_3$ is a bicyclic group it may, for example, be a terpenyl bicyclic group, such as a norbornyl group; when $R_3$ represents an aryl group it may, for example, be a phenyl group; when $R_3$ represents a cycloalkyl or cycloaliphatic alkyl group it may, for example, contain from 3 to 6 carbon atoms; when $R_3$ represents a heterocyclic group it may, for example, be an unsaturated six-membered ring, such as pyridyl; when $R_3$ and $R_2$, together with the adjacent nitrogen atom represent a heterocyclic group this may, for example, be a saturated five or six-membered ring which may contain a further heteroatom, such as pyrrolidine or morpholine; when $R_4$ represents an alkyl or alkoxy group having 1 to 4 carbom atoms it may, for example, be methyl or methoxy; when $R_4$ represents a halogen atom it may, for example, be a chlorine atom; when Het represents a substituted or unsubstituted heterocyclic group containing two or three heteroatoms it may, for example, be a five-membered ring, such as a thiazole, oxazole, 1,3,4-thiadiazole, 1,2,4-thiadiazole or 1,2,4-oxadiazole ring. In the above-mentioned formula the amidine radical may be in the ortho-, meta- or para-position on the benzene ring with respect to the Het group, and the group $R_4$ may be in any position on the benzene ring.

Preferred compounds according to the present invention are those wherein the amidine radical is in the meta-position on the benzene ring, R, $R_1$ and $R_4$ are hydrogen, $R_2$ is absent, $R_3$ is methyl, ethyl, n-propyl, isopropyl, n-butyl, isobutyl, sec-butyl, neopentyl, n-hexyl, n-octyl, allyl, dimethylallyl, propargyl, cyclopropylmethyl, cychexyl, norbornyl, phenyl, pyridyl, hydroxypropyl, methoxyethyl, methylthioethyl or cyanoethyl, Het is thiazolyl or 1,2,4-thiadiazolyl, and their physiologically compatible acid addition salts. Such compounds generally have better activity and are therefore preferred as antisecretory-antiulcerogenic agents and for the treatment of disorders of the gastro-intestinal tract.

The compounds of the formula I may, for example, be prepared by the following methods which constitute further features of the invention.

Method A

Reaction of a guanidino-heterocyclyl-phenylamine of the formula

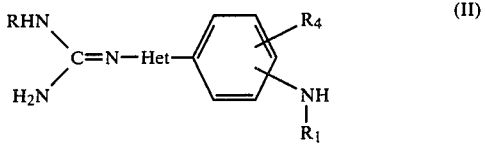

(II)

in which R, $R_1$, $R_4$ and Het have the meanings previously defined, with a reactive derivative of a carboxamide of the formula

(III)

where $R_3$ has the meanings previously defined, and A represents a lower alkoxy group such as methoxy or ethoxy. The reaction is generally carried out at a temperature from 0° to 100° C., preferably from 20° to 60° C. The reaction is advantageously carried out in the presence of an inert organic solvent, for example in an alcohol having from 1 to 3 carbon atoms such as methanol or ethanol, a halogenated hydrocarbon such as dichloromethane, or in dioxane or acetone.

The starting compounds of the formula III may be prepared by conventional methods, that is, reacting an amine of the formula

(IV)

wherein $R_2$ and $R_3$ have the meanings previously defined, with a compound of the formula

(V)

wherein Y is a lower alkyl group, such as methyl or ethyl, in the presence of a mineral acid.

Method B

Reaction of an N,N-disubstituted carboxamide dialkyl acetal of the formula

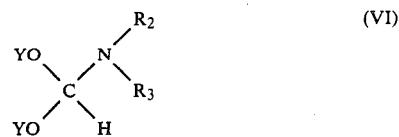

(VI)

in which $R_2$, $R_3$ and Y have the meanings previously defined, with an amine of the formula II. The reaction is carried out at a temperature from 20° to 80° C., and by distilling off the alcohol formed by the reaction.

Method C

Reaction of a novel N,N'-disubstituted amidine of the formula

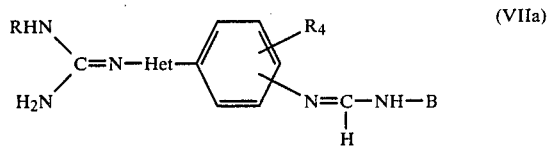

(VIIa)

or

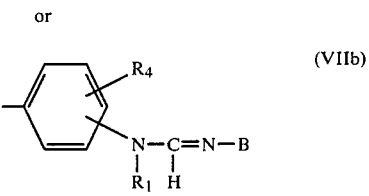

(VIIb)

wherein R, $R_1$, $R_4$ and Het have the meanings previously defined, and B is a leaving group such as cyano, acetyl, carbethoxy or carbamyl, with an amine of the formula IV.

The reaction is advantageously performed in the presence of water or of an inert organic solvent, for example a lower alcohol such as methanol or ethanol, formamide, dimethylformamide, dioxane or acetonitrile. The reaction is generally carried out at a temperature from 10° to 50° C., preferably at room temperature.

The starting compounds of the formulas VIIa and VIIb are obtained by methods described in the literature, for example by reacting an amine of the formula II with an N-substituted alkyl imidate of the formula

(VIII)

in which Y and B have the meanings previously defined, or optionally, when B in the compounds of the formulas VIIa and VIIb represents a cyano group, the reaction may also be performed in a single step by reacting an amine of the formula II with cyanamide in the presence of a compound of the formula V. The reaction is generally carried out in a suitable solvent such as lower alcohol, an ether, ethyl acetate, acetonitrile of dioxane, or without a solvent at a temperature from 20° to 80° C.

The compounds of the formula VIII may be prepared by conventional methods.

The compounds of the formula I are basic and therefore form acid addition salts with inorganic or organic acids. Examples of non-toxic, pharmacologically acceptable acid addition salts are those formed with hydrochloric acid, nitric acid, sulfuric acid, maleic acid, fumaric acid, citric acid, tartaric acid or the like by conventional methods, such as by reacting the free base with a solution of the corresponding acid in a suitable solvent. Particularly preferred acids are hydrochloric, sulfuric, maleic and fumaric acid.

Particularly preferred compounds of the present invention are the following:
N-Methyl-N'-[3-(2-guanidino-4-thiazolyl)-phenyl]-formamidine,
N-Ethyl-N'-[3-(2-guanidino-4-thiazolyl)-phenyl]-formamidine,
N-Propyl-N'-[3-(2-guanidino-4-thiazolyl)-phenyl]-formamidine,
N-Isopropyl-N'-[3-(2-guanidino-4-thiazolyl)-phenyl]-formamidine,
N-Butyl-N'-[3-(2-guanidino-4-thiazolyl)-phenyl]-formamidine,
N-sec.Butyl-N'-[3-(2-guanidino-4-thiazolyl)-phenyl]-formamidine,
N-Isobutyl-N'-[3-(2-guanidino-4-thiazolyl)-phenyl]-formamidine,
N-Allyl-N'-[3-(2-guanidino-4-thiazolyl)-phenyl]-formamidine,
N-Propargyl-N'-[3-(2-guanidino-4-thiazolyl)-phenyl]-formamidine,
N-(2-Methoxyethyl)-N'-[3-(2-guanidino-4-thiazolyl)-phenyl]-formamidine,
N-(3-Hydroxypropyl)-N'-[3-(2-guanidino-4-thiazolyl)-phenyl]-formamidine,
N-Ethyl-N'-[3-(5-guanidino-1,2,4-thiadiazol-3-yl)-phenyl]-formamidine,
and their non-toxic, pharmacologically acceptable acid addition salts.

The following examples illustrate the present invention and will enable others skilled in the art to understand it more completely. It should be understood, however, that the invention is not limited to the particular examples given below.

Preparation of starting compounds:

EXAMPLE 1

Ethyl N-[3-(2-bromo-acetyl)-phenyl]-carbamate 24.1 gm of bromine were added slowly over a period of 30 minutes to a stirred suspension of 28.5 gm of ethyl N-(3-acetyl-phenyl)-carbamate in 13.3 gm of dry dioxane and 245 ml of dry ether. After stirring the reaction solution for 2 hours more, it was cooled, and the product which crystallized out was collected and washed with ether, yielding 38.5 gm of the title compound, m.p. 108°–110° C.

EXAMPLE 2

Ethyl-N-[3-2-guanidino-4-thiazolyl)-phenyl]-carbamate hydrobromide

A mixture of 17.17 gm of ethyl N-[3-(2-bromoacetyl)-phenyl]-carbamate, 7.1 gm of amidinothiourea and 45 ml of ethanol was refluxed for 4 hours and then cooled to room temperature. The precipitate formed thereby was filtered off and washed with cold ethanol, yielding 22 gm of the title compound, m.p. 240°-2° C.

Following the above procedure, using the appropriate bromoacetyl starting materials, the following carbamates were also prepared:
Ethyl N-[4-(2-guanidino-4-thiazolyl)-phenyl]-carbamate hydrobromide, m.p. 254° C. (dec.), and
Ethyl N-[3-(2-methylguanidino-4-thiazolyl)-phenyl]-carbamate hydrobromide, m.p. 231°–233° C.

EXAMPLE 3

2-Guanidino-4-(3-aminophenyl)thiazole

A mixture of 47.1 gm of ethyl N-[3-(2-guanidino-4-thiazolyl)-phenyl]-carbamate hydrobromide, 210 ml of ethanol and 210 ml of a 50% potassium hydroxide solution was refluxed for 15 minutes. After cooling, the white precipitate which had formed was filtered off, dissolved in water and carefully acidified with hydrochloric acid. The resulting solution was made alkaline with an excess of sodium hydroxide solution, and the precipitate formed thereby was filtered off, washed with water and dried, yielding 20 gm of the title compound, m.p. 222°–224° C.

Following the above procedure, using the appropriate carbamate starting material, the following thiazoles were also prepared:
 (a) 2-Guanidino-4-(4-amino-phenyl)thiazole, m.p. 251°–253° C.
 (b) 2-(2-Methyl-guanidino)-4-(3-amino-phenyl)-thiazole, m.p. 180°–182° C.

Preparation of end products of the formula I:

EXAMPLE 4

N-Cyano-N'-[3-(2-guanidino-4-thiazolyl)-phenyl]-formamidine (a) A solution of 9.33 gm of 2-guanidino-4-(3-aminophenyl)-thiazole and 3.93 gm of ethyl N-cyano-formamidate in 65 ml of ethanol was stirred at room temperature overnight. The crystalline product which separated out was collected by filtration, washed with cold ethanol and dried, yielding 9.2 gm of the title compound, mp. 215° C. (dec.)

(b) A mixture of 23.3 gm of 2-guanidino-4-(3-aminophenyl)-thiazole, 18.5 gm of ethyl ortoformate and 4.2 gm of cyanamide was heated at 120° C. for 15 minutes, cooled to room temperature, treated with ethanol and filtered, yielding 23 gm of the title compound, m.p. 214°–216° C. (dec.).

Following the above procedures, using the appropriate amine starting material, the following N-cyano-amidines were also prepared:
 (c) N-Cyano-N'-[4-(2-guanidino-4-thiazolyl)-phenyl]-formamidine, m.p. 240° C. (dec.);
 (d) N-Cyano-N'-[2-(2-guanidino-4-thiazolyl)-phenyl]-formamidine, m.p. 174° C. (dec.);
 (e) N-Cyano-N'-[3-(2-methyl-guanidino-4-thiazolyl)-phenyl]-formamidine, m.p. 218°–220° C.;
 (f) N-Cyano-N'-methyl-N'-[3-(2-guanidino-4-thiazolyl)-phenyl]-formamidine, m.p. 216°–217° C. (dec.);
 (g) N-Cyano-N'-[3-(2-guanidino-5-methyl-4-thiazolyl)-phenyl]-formamidine, m.p. 180° C., (dec.);
 (h) N-Cyano-N'-[6-methyl-3-(2-guanidino-4-thiazolyl)-phenyl]-formamidine, m.p. 245°–248° C.;
 (i) N-Cyano-N'-[5-chloro-3-(2-guanidino-4-thiazolyl)-phenyl]-formamidine, m.p. 265°–267° C., (dec.);
 (j) N-Cyano-N'-[6-methoxy-3-(2-guanidino-4-thiazolyl)-phenyl]-formamidine, m.p. 248°–250° C. (dec.);
 (k) N-Cyano-N'-[4-(2-guanidino-1,3,4-thiadiazol-5-yl)-phenyl]-formamidine, m.p. 248°–250° (dec.);
 (l) N-Cyano-N'-[3-(2-guanidino-1,3,4-thiadiazol-5-yl)-phenyl]-formamidine, m.p. 259°–261° (dec.);
 (m) N-Cyano-N'-[3-(5-guanidino-1,2,4-thiadiazol-3-yl)-phenyl]-formamidine, m.p. 265°–268° (dec.);

(n) N-Cyano-N'-[4-(5-guanidino-1,2,4-thiadiazol-3-yl)-phenyl]-formamidine, m.p. 253°–255° C. (dec.);
(o) N-Cyano-N'-[3-(2-guanidino-4-oxazolyl)-phenyl]-formamidine, m.p. 225°–226° C.;
N-Cyano-N'-[4-(2-guanidino-4-oxazolyl)-phenyl]-formamidine, m.p. 222°–223° C.;
(q) N-Cyano-N'-[4-(5-guanidino-1,2,4-oxadiazol-3-yl)-phenyl]-formamidine, m.p. >270° C.; and
(r) N-Cyano-N'-[3-(5-guanidino-1,2,4-oxadiazol-3-yl)-phenyl]-formamidine, m.p. 246°–248° C.

Preparation of starting compounds:

EXAMPLE 5

5-Guanidino-3-(3-nitrophenyl)1,2,4-oxadiazole 7.3 gm of guanidine hydrochloride were added in portions to a solution of 1.8 gm of sodium in 100 ml of ethanol. After 30 minutes of stirring, 22.5 gm of 3-(3-nitro-phenyl)-5-trichloromethyl-1,2,4-oxadiazole were added. The solid which separated out overnight was filtered off and dried, yielding 15.2 gm of the title compound, m.p. 290°–291° C.

EXAMPLE 6

2-Guanidino-4-(4-nitro-phenyl)-oxazole hydrochloride

A solution of 90 gm of 4-nitro-phenacyl acetate and 33.9 gm of 1-cyano-guanidine in 200 ml of dioxane and 20 ml of 5N hydrochloric acid was stirred for 2 days at room temperature. A first crop of the product was filtered off; the solution, after the addition of another 40 ml of 5N hydrochloric acid, was stirred for 3 days and furnished a second crop of the product. The total yield of the title compound was 46 gm, m.p. >285° C.

EXAMPLE 7

2-Guanidino-4-(2-nitro-phenyl)-thiazole

A solution of 16.5 gm of 2-nitro-phenacyl bromide and 7.98 gm of amidinothiourea in 70 ml of dimethylformamide was stirred at room temperature for 16 hours, and then poured into 350 ml of water. The solution was made alkaline with 10% sodium hydroxide, and the solid which separated out after cooling was filtered, washed with water and dried, yielding 16.9 gm of the title compound, m.p. 176°–178° C.

Following the above procedure, using the appropriate phenacyl bromide as starting material, the following nitrophenyl-thiazole derivatives were also prepared:
(a) 2-Guanidino-4-(4-methyl-3-nitro-phenyl)-thiazole, m.p. 225°–227° C.;
(b) 2-Guanidino-4-(4-chloro-3-nitro-phenyl)-thiazole, m.p. 248°–250° C.; and
(c) 2-Guanidino-4-(4-methoxy-3-nitro-phenyl)-thiazole, m.p. 236°–238° C.

EXAMPLE 8

2-Guanidino-4-(2-amino-phenyl)-thiazole

A solution of 57 gm of sodium sulfide octahydrate in 400 ml of methanol and 120 ml of water was added dropwise over a period of 30 minutes to a hot (60° C.) solution of 16.9 gm of 2-guanidino-4-(2-nitro-phenyl)-thiazole in 120 ml of methanol. After an additional 2 hours of heating at 60° C., the solution was filtered with charcoal and evaporated to dryness. The residual solid was suspended in water, filtered off and dried, yielding 12.4 gm of the title compound, m.p. 198°–200° C.

Following the above procedure, using the appropriate nitrophenyl derivative, the following aminophenyl derivatives were also prepared:
(a) 2-Guanidino-4-(3-amino-4-methyl-phenyl)-thiazole, m.p. 251°–252° C.;
(b) 2-Guanidino-4-(3-amino-4-chloro-phenyl)-thiazole, m.p. 245°–248° C.;
(c) 2-Guanidino-4-(3-amino-4-methoxy-phenyl)-thiazole, m.p. 157°–159° C.;
(d) 2-Guanidino-5-(4-amino-phenyl)-1,3,4-thiadiazole, m.p. 274°–275° C.;
(e) 2-Guanidino-5-(3-amino-phenyl)-1,3,4-thiadiazole, m.p. 244°–247° C.;
(f) 5-Guanidino-3-(4amino-phenyl)-1,2,4-thiadiazole, m.p. 282°–284° C. (as hydrochloride);
(g) 2-Guanidino-4-(4-amino-phenyl)-oxazole, m.p. 212°–213° C.;
(h) 5Guanidino-3-(4-amino-phenyl)-1,2,4-oxadiazole, m.p. 245° C. (dec.); and
(i) 5-Guanidino-3-(3-amino-phenyl)-1,2,4-oxadiazole, m.p. 260° C. (dec.).

EXAMPLE 9

2-Guanidino-5-(4-nitro-phenyl)-1,3,4-thiadiazole 24.13 gm of guanidine nitrate were added in small portions over a period of 30 minutes to 6.5 gm of a 50% sodium hydride oil dispersion in 200 ml of dimethylformamide. After the evolution of hydrogen had ceased, a solution 15.8 gm of 2-chloro-5-(4-nitro-phenyl)-1,3,4-thiadiazole in 300 ml of dimethylformamide was added dropwise to the mixture, which was then stirred at room temperature for 2 hours, and then at 90° C. for 30 minutes. After cooling and dilution with water, the precipitate formed thereby was filtered off and dissolved in ethanol. Hydrogen chloride was added to this solution, and the hydrochloride which separated out was filtered off and dissolved in water, and then aqueous solution was made alkaline with 10% sodium hydroxide. The free base was filtered off, washed with water and dried, yielding 9.5 gm of the title compound, m.p. 295°–297° C.

Following the above procedure, using the appropriate thiadiazole derivative as starting material, the following compounds were also prepared:
(a) 2-Guanidino-5-(3-nitro-phenyl)-1,3,4-thiadiazole, m.p. 296°–298° C.; and
(b) 5-Guanidino-3-(4-nitro-phenyl)-1,2,4-thiadiazole, m.p. 272°–275° C.

EXAMPLE 10

2-Chloro-5-(3-nitro-phenyl)-1,3,4-thiadiazole

A mixture of 14.8 gm of 2-amino-5-(3-nitro-phenyl)-1,3,4-thiadiazole and 20.67 gm of sodium nitrite was added to 25% hydrochloride acid (120 ml), cooled at −10° C. and containing a small amount of Cu powder over a period of 20 minutes.

The resulting solution was stirred at −5° C. for one hour and at room temperature for 90 minutes and was then neutralized with 10% sodium hydroxide. After addition of sodium metabisulfite solution, the mixture was heated at 60° C. for 10 minutes, filtered, and the solid was extracted with chloroform. The organic solution was evaporated to dryness, yielding 12 gm of the title compound, m.p. 162°–165° C.

EXAMPLE 11

5-Chloro-3-(4-nitro-phenyl)-1,2,4-thiadiazole

A solution of 75.6 gm of sodium hydroxide in 100 ml of water was added to a stirred mixture of 101.4 gm of p-nitrobenzamidine hydrochloride, 70 gm of perchloromethyl mercaptan and 760 ml of dichloromethane, while keeping the temperature below −5° C. After additional 2 hours at −5° C., the resulting suspension was filtered, and the organic phase was separated, evaporated to dryness, and the residual solid was recrystallized from 95% ethanol, yielding 45 gm of the title compound, m.p. 143°–145° C.

EXAMPLE 12

3-Methylamino-phenacyl bromide hydrobromide

(a) 3-Acetylphenyliminotriphenyl phosphorane

A mixture of 67.6 gm of 3-amino acetophenone, 101.2 gm of triethylamine and 100 ml of carbon tetrachloride was added to a stirred suspension of 211 gm of triphenylphosphine dibromide in 1700 ml of carbon tetrachloride. After 20 minutes of refluxing, the mixture was filtered and evaporated to dryness. The residual solid was treated with isopropanol, filtered and dried, yielding 140.2 gm of the title compound, m.p. 135°–136° C.

(b) [N-Methyl-N-(3-acetyl-phenyl)-amino]-triphenyl phosphonium iodide

A solution of 140.2 gm of 3-acetylphenyliminotriphenyl phosphorane and 56.9 gm of methyl iodide in 525 ml of dry benzene was refluxed for 8 hours in an atmosphere of nitrogen. The mixture was cooled, and the precipitate was filtered off, washed with benzene and dried, yielding 120 gm of the title compound, m.p. 178°–180° C.

(c) 3-Methylamino-acetophenone

A mixture of 120 gm of [N-methyl-N-(3-acetyl-phenyl)-amino]-triphenyl phosphonium iodide and 2250 ml of 2N sodium hydroxide was refluxed for one hour. The mixture was then cooled, acidified with hydrochloric acid, and extracted with dichloromethane. The aqueous solution was made strongly alkaline with sodium hydroxide solution, and the amine which separated out was extracted with diethyl ether. After removal of the solvent, the residue was distilled, yielding 25 gm of the title compound, b.p. 102°–103° C. (0.05 mmHg).

(d) 3-Methylamino-phenacyl bromide hydrobromide

A solution of 26.8 gm of bromine in 20 ml of glacial acetic acid was added to a solution of 25 gm of 3-methylamino-acetophenone and 16.1 gm of methanesulfonic acid in 200 ml of glacial acetic acid. After 12 hours of stirring with ultraviolet light irradiation, the mixture was treated with 30 ml of a solution of 30% anhydrous hydrogen bromide in acetic acid, and then diluted with about 5 vol. of ether. The precipitate was filtered off, washed with ether and recrystallized from absolute ethanol, yielding 20 gm of the title compound, m.p. 174°–176° C. (dec.).

EXAMPLE 13

2-Guanidino-4-(3-methylamino-phenyl)-thiazole

A mixture of 20 gm of 3-methylamino phenacyl bromide hydrobromide, 7.65 gm of amidinothiourea and 100 ml of ethanol was refluxed for 4 hours, and then cooled to room temperature. The dihydrobromide which separated out was filtered off, dissolved in water, and the solution was made alkaline with 10% sodium hydroxide. The free base was collected and dried, yielding 11.5 gm of the title compound, m.p. 198°–200° C.

Preparation of end products of the formula I:

EXAMPLE 14

N-Methyl-N'-[3-(2-guanidino-4-thiazolyl)-phenyl]-formamidine 4 gm of N-cyano-N'-[3-(2-guanidino-4-thiazolyl)-phenyl]-formamidine were added all at once to 40 ml of 35% methylamine in water (40 ml). A few minutes later, the reaction product separated out of the solution. This solid was filtered, washed with water and dried, yielding 2.66 gm of the title compound.

Maleate salt (ethanol): M.p. 182° C. (dec.).

Analysis: $C_{20}H_{22}N_6O_8S$, Found %: C 46.98, H 4.32, N 16.41, Cal. %: C 47.43, H.4.38, N 16.59.

The following compounds were prepared in analogous manner, starting from the above N-cyano-formamidine derivative.

(a) N-Ethyl-N'-[3-(2-guanidino-4-thiazolyl)phenyl]-formamidine

Maleate salt, (ethanol): M.p. 175°–177° C. (dec.).

Analysis: $C_{21}H_{24}N_6O_8S$, Found %: C 47.95, H 4.70, N 15.98, Calc. %: C 48.46, H 4.65, N 16.14.

(b) N-Propyl-N'-[3-(2-guanidino-4-thiazolyl)-phenyl]-formamidine

Maleate salt (ethanol): M.p. 180° C. (dec.).

Analysis: $C_{22}H_{26}N_6O_8S$, Found %: C 49.43, H 4.88, N 15.59, Calc. %: C 49.43, H 4.90, N 15.72.

(c) N-Isopropyl-N'-[3-(2-guanidino-4-thiazolyl)-phenyl]-formamidine

Citrate salt (ethanol): M.p. 135° C. (dec.).

Analysis: $C_{46}H_{60}N_{12}O_{21}S_2$, Found %: C 46.96, H 5.18, N 14.32, Calc. %: C 46.78, H 5.12, N 14.23.

(d) N-Butyl-N'-[3-(2-quanidino-4-thiazolyl)-phenyl]-formamidine

Maleate salt (ethanol): M.p. 196° C. (dec.).

Analysis: $C_{23}H_{28}N_6O_8S$, Found %: C 49.86, H 5.03, N 15.21, Calc. %: C 50.36, H 5.14, N 15.32.

(e) N-sec.Butyl-N'-[3-(2-guanidino-4-thiazolyl)-phenyl]-formamidine

Maleate salt (ethanol): M.p. 190° C. (dec.).

Analysis: $C_{23}H_{28}N_6O_8S$, Found %: C 49.81, H 5.18, N 15.02, Calc. %: C 50.36, H 5.14, N 15.32.

(f) N-Isobutyl-N'-[3-(2-guanidino-4-thiazolyl)-phenyl]-formamidine

Maleate salt (ethanol): M.p. 208° C. (dec.).

Analysis: $C_{23}H_{28}N_6O_8S$, Found %: C 50.16, H 5.16, N 15.33, Calc %: C 50.36, H 5.14, N 15.32.

(g)
N-Neopentyl-N'-[3-(2-guanidino-4-thiazolyl)-phenyl]-formamidine

Maleate salt (ethanol): M.p. 187°–190° C. (dec.).
Analysis: $C_{24}H_{30}N_6O_8S$, Found %: C 50.73, H 5.33, N 14.81, Calc. %: C 51.24, H 5.37, N 14.94.

(h)
N-Hexyl-N'-[3-(2-guanidino-4-thiazolyl)-phenyl]-formamidine

Maleate salt (ethanol): M.p. 196° C. (dec.).
Analysis: $C_{25}H_{32}N_6O_8S$, Found %: C 51.71, H 5.65, N 14.70, Calc. %: C 52.07, H 5.59, N 14.57.

(i)
N-Octyl-N'-[3-(2-guanidino-4-thiazolyl)-phenyl]-formamidine

Maleate salt (ethanol): M.p. 177°–180° C. (dec.).
Analysis: $C_{27}H_{36}N_6O_8S$, Found %: C 53.15, H 6.00, N 13.86, Calc. %: C 53.63, H 6.00, N 13.89.

(j)
N-Allyl-N'-[3-(2-guanidino-4-thiazolyl)-phenyl]-formamidine

Maleate salt (ethanol): M.p. 168°–170° C. (dec.).
Analysis: $C_{22}H_{24}N_6O_8S$, Found %: C 49.19, H 4.47, N 15.50, Calc. %: C 49.62, H 4.54, N 15.78.

(k)
N-Dimethylallyl-N'-[3-(2-guanidino-4-thiazolyl)-phenyl]-formamidine

Maleate salt (ethanol): M.p. 163° C. (dec.).
Analysis: $C_{24}H_{28}N_6O_8S$, Found %: C 51.12, H 4.98, N 14.64, Calc. %: C 51.42, H 5.03, N 14.99.

(l)
N-Propargyl-N'-[3-(2-guanidino-4-thiazolyl)-phenyl]-formamidine

Maleate salt (ethanol): M.p. 170° C. (dec.).
Analysis: $C_{22}H_{22}N_6O_8S$, Found %: H 49.06, H 4.12, N 15.89, Calc. %: C 49.81, H 4.18, N 15.84.

(m)
N-Cyclopropylmethyl-N'-[3-(2-guanidino-4-thiazolyl)-phenyl]-formamidine

Maleate salt (ethanol): M.p. 183°–185° C. (dec.).
Analysis: $C_{23}H_{26}N_6O_8S$, Found %: C 49.82, H 4.71, N 15.28, Calc. %: C 50.54, H 4.79, N 15.38.

(n)
N-Cyclohexyl-N'-[3-(2-guanidino-4-thiazolyl)-phenyl]-formamidine

Maleate salt (ethanol): M.p. 190° C. (dec.).
Analysis: $C_{25}H_{30}N_6O_8S$, Found %: C 52.00, H 5.34, N 14.81, Calc. %: C 52.26, H 5.26, N 14.63.

(o)
N-Norbornyl-N'-[3-(2-guanidino-4-thiazolyl)-phenyl]-formamidine

Maleate salt (ethanol): M.p. 196° C. (dec.).
Analysis: $C_{26}H_{30}N_6O_8S$, Found %: C 53.15, H 5.22, N 14.21, Calc. %: C 53.23, H 5.15, N 14.33.

(p)
N-(2-Methoxy-ethyl)-N'-[3-(2-guanidino-4-thiazolyl)-phenyl]-formamidine

Maleate salt (ethanol): M.p. 182°–184° C. (dec.).
Analysis: $C_{22}H_{26}N_6O_9S$, Found %: C 47.67, H 4.71, N 15.15, Calc. %: C 48.00, H 4.76, N 15.26.

(q)
N-(2-Methylthio-ethyl)-N'-[3-(2-guanidino-4-thiazolyl)-phenyl]-formamidine

Maleate salt (ethanol): M.p. 180°–183° C. (dec.).
Analysis: $C_{22}H_{26}N_6O_8S_2$, Found %: C 46.13, H 4.57, N 14.71, Calc. %: C 46.63, H 4.62, N 14.83.

(r)
N-(2-Cyano-ethyl)-N'-[3-(2-guanidino-4-thiazolyl)-phenyl]-formamidine

Maleate salt (ethanol): M.p. 160°–164° C. (dec.).
Analysis: $C_{22}H_{23}N_7O_8S$, Found %: C 48.03, H 4.16, N 18.15, Calc. %: C 48.44, H 4.25, N 17.97.

(s)
N-(3-Hydroxy-propyl)-N'-[3-(2-guanidino-4-thiazolyl)-phenyl]-formamidine

Maleate salt (ethanol): M.p. 184° C. (dec.).
Analysis: $C_{22}H_{26}N_6O_9S$, Found %: C 47.08, H 4.57, N 16.95, Calc. %: C 46.98, H 4.66, N 17.06.

(t)
N-Methyl-N'-[4-(2-guanidino-4-thiazolyl)-phenyl]-formamidine

Hydrochloride salt (ethanol): M.p. 264° C. (dec.).
Analysis: $C_{12}H_{16}Cl_2N_6S$, Found %: C 41.25, H 4.55, N 24.31, Calc. %: C 41.50, H 4.64, N 24.20.

(u)
N-Ethyl-N'-[4-(2-guanidino-4-thiazolyl)-phenyl]-formamidine

Fumarate salt (ethanol): M.p. 136° C. (dec.).
Analysis: $C_{21}H_{24}N_6O_8S$, Found %: C 48.37, H 4.85, N 16.16, Calc. %: C 48.46, H 4.65, N 16.14.

(v)
N-Isopropyl-N'-[4-(2-guanidino-4-thiazolyl)-phenyl]-formamidine, m.p. 249°–250° C. (dec.).

Analysis: $C_{14}H_{18}N_6S$, Found %: C 56.07, H 6.04, N 27.32, Calc. %: C 55.61, H 6.00, N 27.79.

(w)
N-Ethyl-N'-[2-(2-guanidino-4-thiazolyl)-phenyl]-formamidine

Tartrate salt (ethanol): M.p. 110° C. (dec.).
Analysis: $C_{38}H_{50}N_{12}O_{18}S_2$, Found %: C 44.03, H 5.14, N 16.67, Calc. %: C 44.44, H 4.91, N 16.36.

(x)
N-Propyl-N'-[2-(2-guanidino-4-thiazolyl)-phenyl]-formamidine

Tartrate salt (ethanol): M.p. 135° C. (dec.).
Analysis: $C_{40}H_{54}N_{12}O_{18}S_2$, Found %: C 45.53, H 5.20, N 15.70, Calc. %: C 45.53, H 5.16, N 15.93.

(y)
N-Allyl-N'-[2-(2-guanidino-4-thiazolyl)-phenyl]-formamidine

Tartrate salt (ethanol) M.p. 120° C. (dec.).
Analysis: $C_{40}H_{50}N_{12}O_{18}S_2$, Found %: C 45.51, H 4.68, N 16.12, Calc. %: C 45.71, H 4.79, N 15.99.

(z)
N-Ethyl-N'-[3-(2-methylguanidino-4-thiazolyl)-phenyl]-formamidine

Maleate salt (ethanol): M.p. 183° C. (dec.).
Analysis: $C_{22}H_{26}N_6O_8S$, Found %: C 49.12, H 4.94, N 15.59, Calc. %: C 49.43, H 4.90, N 15.72.

(aa)
N-Propyl-N'-[3-(2-methylguanidino-4-thiazolyl)-phenyl]-formamidine

Maleate salt (ethanol): M.p. 172° C. (dec.).
Analysis: $C_{23}H_{28}N_6O_8S$, Found %: C 50.51, H 5.11, N 15.45, Calc. %: C 50.36, H 5.14, N 15.32.

(ab)
N-Isopropyl-N'-[3-(2-methylguanidino-4-thiazolyl)-phenyl]-formamidine

Maleate salt (ethanol): M.p. 95° C. (dec.).
Analysis: $C_{23}H_{28}N_6O_8S$, Found %: C 50.25, H 5.16, N 15.10, Calc. %: C 50.36, H 5.14, N 15.32.

(ac)
N,N-Dimethyl-N'-[3-(2-guanidino-4-thiazolyl)-phenyl]-formamidine

Maleate salt (ethanol): M.p. 216° C. (dec.).
Analysis: $C_{21}H_{24}N_6O_8S$, Found %: C 48.61, H 4.70, N 16.26, Calc. %: C 46.46, H 4.65, N 16.15.

(ad)
N,N-Diethyl-N'-[3-(2-guanidino-4-thiazolyl)-phenyl]-formamidine

Maleate salt (ethanol): M.p. 190°-193° C. (dec.).
Analysis: $C_{23}H_{28}N_6O_8S$, Found %: C 49.99, H 5.06, N 15.32, Calc. %: C 50.36, H 5.14, N 15.32.

(ae)
N-[3-(2-guanidino-4-thiazolyl)-phenyl]-1-pyrrolidinyl-methanimine

Maleate salt (ethanol): M.p. 197°-199° C. (dec.).
Analysis: $C_{23}H_{26}N_6O_8S$, Found %: C 50.87, H 4.86, N 15.08, Calc. %: C 50.54, H 4.79, N 15.38.

(af)
N-[3-(2-guanidino-4-thiazolyl)-phenyl]-4morpholinyl-methanimine

Maleate salt (ethanol): M.p. 208°-210° C. (dec.).
Analysis: $C_{23}H_{26}N_6O_9S$, Found %: C 48.88, H 4.70, N 15.05, Calc. %: C 49.10, H 4.66, N 14.94.

(ag)
N-Propyl-N'-methyl-N'-[3-(2-guanidino-4-thiazolyl)-phenyl]-formamidine

Maleate salt (ethanol): M.p. 105°-106° C. (dec.).
Analysis: $C_{23}H_{28}N_6O_8S$, Found %: C 50.21, H 4.99, N 15.45, Calc. %: C 50.36, H 5.14, N 15.32.

(ah)
N-Ethyl-N'-[3-(2-guanidino-5-methyl-4-thiazolyl)-phenyl]-formamidine

Maleate salt (ethanol): M.p. 155° C. (dec.).
Analysis: $C_{22}H_{26}N_6O_8S$, Found %: C 49.19, H 4.82, N 15.43, Calc. %: C 49.43, H 4.90, N 15.72.

(ai)
N-Propyl-N'-[3-(2-guanidino-5methyl-4-thiazolyl)-phenyl]-formamidine

Maleate salt (ethanol): M.p. 160° C. (dec.).
Analysis: $C_{23}H_{28}N_6O_8S$, Found %: C 49.86, H 4.93, N 15.52, Calc. %: C 50.36, H 5.14, N 15.32.

(aj)
N-Propyl-N'-[6-methyl-3-(2-guanidino-4-thiazolyl)-phenyl]-formamidine

Maleate salt (ethanol): M.p. 204°-207° C. (dec.).
Analysis: $C_{23}H_{28}N_6O_8S$, Found %: C 50.00, H 5.25, N 15.45, Calc. %: C 50.36, H 5.15, N 15.32.

(ak)
N-Propyl-N'-[6-chloro-3-(2-guanidino-4-thiazolyl)-phenyl]-formamidine

Maleate salt (ethanol): M.p. 192°-195° C. (dec.).
Analysis: $C_{22}H_{25}ClN_6O_8S$, Found %: C 46.74, H 4.51, N 14.54, Calc. %: C 46.44, H 4.43, N 14.77.

(al)
N-Propyl-N'-[6-methoxy-3-(2-guanidino-4-thiazolyl)-phenyl]-formamidine

Maleate salt (ethanol): M.p. 201°-204° C. (dec.).
Analysis: $C_{23}H_{28}N_6O_9S$, Found %: C 49.19, H 5.07, N 14.74, Calc. %: C 48.93, H 4.99, N 14.89.

(am)
N-Ethyl-N'-[4-(2-guanidino-1,3,4-thiadiazol-5-yl)-phenyl]-formamidine

Maleate salt (acetone): M.p. 182°-183° C. (dec.).
Analysis: $C_{20}H_{23}N_7O_8S$, Found %: C 46.18, H 4.49, N 18.70, Calc. %: C 46.06, H 4.45, N 18.80.

(an)
N-Isopropyl-N'-[4-(2-guanidino-1,3,4-thiadiazol-5-yl)-phenyl]-formamidine Maleate salt (ethanol): M.p. 178° C. (dec.).
Analysis: $C_{21}H_{25}N_7O_8S$, Found %: C 46.95, H 4.77, N 18.42, Calc. %: C 47.09, H 4.71, N 18.31.

(ao)
N-Isopropyl-N'-[3-(2-guanidino-1,3,4-thiadiazol-5-yl)-phenyl]-formamidine Maleate salt (acetone): M.p. 166° C. (dec.).
Analysis: $C_{21}H_{25}N_7O_8S$, Found %: C 46.75, H 4.68, N 18.35, Calc. %: C 47.09, H 4.71, N 18.31.

(ap)
N-Ethyl-N'-[3-(5-guanidino-1,2,4-thiadiazol-3-yl)-phenyl]-formamidine

Maleate salt (ethanol): M.p. 173°-175° C. (dec.).
Analysis: $C_{20}H_{23}N_7O_8S$, Found %: C 45.92, H 4.50, N 18.69, Calc. %: C 46.06, H 4.45, N 18.80.

(aq)
N-Isopropyl-N'-[3-(5-guanidino-1,2,4-thiadiazol-3-yl)-phenyl]-formamidine Maleate salt (ethanol): M.p. 157° C. (dec.).
Analysis: $C_{21}H_{25}N_7O_8S$, Found %: C 46.73, H 4.71, N 18.21, Calc. %: C 47.09, H 4.71, N 18.31.

(ar)
N-Ethyl-N'-[4-(5-guanidino-1,2,4-thiadiazol-3-yl)-phenyl]-formamidine

Maleate salt (acetone): M.p. 184° C. (dec.).
Analysis: $C_{20}H_{23}N_7O_8S$, Found %: C 45.70, H 4.39, N 18.68, Calc. %: C 46.06, H 4.45, N 18.80.

(as)
N-Propyl-N'-[4-(5-guanidino-1,2,4-thiadiazol-3-yl)-phenyl]-formamidine

Maleate salt (acetone): M.p. 187° C. (dec.).
Analysis: $C_{21}H_{25}N_7O_8S$, Found %: C 46.86, H 4.64, N 18.42, Calc. %: C 47.09, H 4.71, N 18.31.

(at)
N-Isopropyl-N'-[4-(5-guanidino-1,2,4-thiadiazol-3-yl)-phenyl]-formamidine Maleate salt (acetone): M.p. 177° C. (dec.).
Analysis: $C_{21}H_{25}N_7O_8S$, Found %: C 46.95, H 4.66, N 18.27, Calc. %: C 47.09, H 4.71, N 18.31.

(au)
N-Methyl-N'-[3-(2guanidino-4-oxazolyl)-phenyl]-formamidine

Hydrochloride salt (ethanol): M.p. 252°–253° C. (dec.).
Analysis: $C_{12}H_{16}Cl_2N_6O$, Found %: C 43.26, H 4.83, N 25.37, Calc. %: C 43.51, H 4.87, N 25.37.

(av)
N-Ethyl-N'-[3-(2quanidino-4-oxazolyl)-phenyl]-formamidine

Hydrochloride salt (ethanol); M.p. 254°–255° C. (dec.).
Analysis: $C_{13}H_{18}Cl_2N_6O$, Found %: C 44.82, H 5.15, N 24.12, Calc. %: C 45.22, H 5.22, N 24.34.

(ax)
N-Hexyl-N'-[3-(2-guanidino-4-oxazolyl)-phenyl]-formamidine

Hydrochloride salt (ethanol): M.p. 237°–238° C. (dec.).
Analysis: $C_{17}H_{26}Cl_2N_6O$, Found %: C 50.17, H 6.57, N 21.09, Calc. %: C 50.87, H 6.53, N 20.94.

(ay)
N-Methyl-N'-[4-(2-quanidino-4-oxazolyl)-phenyl]-formamidine

Hydrochloride salt (ethanol): M.p. 239°–240° C. (dec.).
Analysis: $C_{12}H_{16}Cl_2N_6O$, Found: C 43.25, H 4.87, N 24.91, Calc. %: C 43.51, H 4.87, N 25.37.

(az)
N-Propyl-N'-[4-(2quanidino-4-oxazolyl)-phenyl]-formamidine

Hydrochloride salt (ethanol): M.p. 232°–233° C. (dec.).
Analysis: $C_{14}H_{20}Cl_2N_6O$, Found %: C 47.02, H 5.58, N 23.46, Calc. %: C 46.80, H 5.61, N 23.39.

(ba)
N-Butyl-N'-[4-(2-quanidino-4-oxazolyl)-phenyl]-formamidine

Hydrochloride salt (ethanol): M.p. 233°–235° C. (dec.).
Analysis: $C_{15}H_{22}Cl_2N_6O$, Found %: C 48.41, H 5.99, N 22.14, Calc. %: C 48.26, H 5.94, N 22.52.

(bb)
N-Allyl-N'-[4-(2-guanidino-4-oxazolyl)-phenyl]-formamidine

Fumarate salt (ethanol): M.p. 150°–152° C. (dec.).

Analysis: $C_{18}H_{20}N_6O_5$, Found %: C 53.87, H 5.06, N 21.16, Calc. %: C 53.09, H 5.04, N 20.99.

(bc)
N-Isopropyl-N'-[4-(5-guanidino-1,2,4-oxadiazol-3-yl)-phenyl]-formamidine Maleate salt (ethanol): M.p. 189° C. (dec.).
Analysis $C_{21}H_{25}N_7O_9$, Found %: C 48.10, H 4.86, N 18.61, Calc. %: C 48.55, H 4.85, N 18.87.

(bd)
N-Methyl-N'-[4-(5-guanidino-1,2,4-oxadiazol-3-yl)-phenyl]-formamidine

Fumarate salt (ethanol): M.p. 186°–187° C. (dec.).
Analysis: $C_{15}H_{17}N_7O_5$,
Found %: C 47.85, H 4.57, N 25.91, Calc. %: C 48.00, H 4.57, N 26.12.

(be)
N-Isopropyl-N'-[3-(5-guanidino-1,2,4-oxadiazol-3-yl)-phenyl]-formamidine Maleate salt (ethanol): M.p. 167° C. (dec.).
Analysis: $C_{21}H_{25}N_7O_9$,
Found %: C 48.96, H 4.85, N 19.05, Calc. %: C 48.55, H 4.85, N 18.87.

(bf)
N-Methyl-N'-[3-(5-guanidino-1,2,4-oxadiazol-3-yl)-phenyl]-formamidine

Nitrate salt (methanol): M.p. 215°–216° C. (dec.).
Analysis: $C_{11}H_{15}N_9O_7$, Found %: C 33.97, H 3.88, N 32.58, Calc. %: C 34.28, H 3.92, N 32.72.

(bg)
N-Allyl-N'-[3-(5-guanidino-1,2,4-oxadiazol-3-yl)-phenyl]-formamidine

Maleate salt (ethanol): M.p. 160° C. (dec.).
Analysis: $C_{21}H_{23}N_7O_9$, Found %: C 48.21, H 4.48, N 18.80, Calc. %: C 48.74, H 4.47, N 18.95.

(bh)
N-sec-Butyl-N'-[3-(5-guanidino-1,2,4-oxadiazol-3-yl)-phenyl]-formamidine Maleate salt (ethanol): M.p. 170° C. (dec.).
Analysis: $C_{22}H_{27}N_7O_9$, Found %: C 49.24, H 5.18, N 18.52, Calc. %: C 49.53, H 5.10, N 18.38.

EXAMPLE 15

N,N-Dimethyl-N'-[3-(2-guanidino-4-thiazolyl)-phenyl]-formamidine

A solution of 2.5 gm of 2-guanidino-4-(3-aminophenyl)-thiazole in 7.5 gm of N,N-dimethylformamide diethylacetal was stirred at room temperature for 2 days. Addition of diethyl precipitated a solid which was filtered off and dried, yielding 2.4 gm of the title compound.

Maleate salt: M.p. 214°–215° C. (dec.).

The following formamidine was prepared in analogous manner, starting from N,N-diethylformamide diethylacetal:

(a)     N,N-Diethyl-N'-[3-(2-guanidino-4-thiazolyl)-phenyl]-formamidine

Maleate salt: M.p. 190°–192° C.

EXAMPLE 16

N-(2-Pyridyl)-N'-[3-(2-guanidino-4-thiazolyl)-phenyl]-formamidine 5 gm of 2-guanidino-4-(3-aminophenyl)-thiazole were added to a solution of 9.65 gm of ethyl N-(2-pyridyl)-formamidate in 120 ml of ethanol. After stirring the mixture for 90 minutes at room temperature, the solid which separated out was filtered off and dried, yielding 3 gm of the title compound, m.p. 140° C. (dec.).

Analysis: $C_{16}H_{15}N_7S$. Found %: C 57.14, H 4.41, N 28.86, Calc. %: C 56.96, H 4.48, N 29.06.

The following formamidine was prepared in analogous manner, starting from ethyl N-phenyl formamidate: (a) N-Phenyl-N'-[3-guanidino-4-thiazolyl)phenyl]-formamidine M.p. 167°–168° C. (dec.)

Analysis: $C_{17}H_{16}N_6S$ Found % C 60.10, H 4.74, N 24.56, Calc.% C 60.69, H 4.79, N 24.98.

The compounds of the present invention, that is, those embraced by formula I above and their non-toxic, pharmacologically acceptable acid addition salts, have useful pharmacodynamic properties. More particularly, they exhibit gastric acid secretion inhibiting activity in warm-blooded animals such as rats, and are therefore useful as anti-ulcerogenics.

The antagonistic activity of compounds according to the invention on histamine $H_2$-receptors is demonstrated either in vitro or in vivo by their inhibition of the $H_2$-dependent biological effects, which include the histamine-evoked positive chronotropic effect and the histamine-induced gastric secretion of acid, respectively.

The inhibition of the positive chronotropic effect was investigated in isolated guinea pig atria suspended in an organ bath (50 ml) containing an oxygenated ($O_2$: 95%—$CO_2$: 5%) Krebs-Henseleit solution (pH 7.4) maintained at 32° C. The myocardial preparation, loaded with 1 gm isometric tension, was allowed to stabilize 60 minutes, and myocardial contractions were recorded through an isometric lever connected to a strain-gauge coupler, and the instantaneous rate was monitored with a cardiotachometer and a heat-writing pen recorder. After two control responses to histamine ($10^{-6}$ g/ml) the test compound was added to the bath at the desired final concentration and left for 30 minutes before the atria were again challenged with histamine. The chronotropic obtained in the presence of the antagonist was then compared to the control response to histamine, and the percent reduction of the histamine $H_2$-evoked response was calculated. The average effective concentration ($EC_{50}$) of the $H_2$-antagonist was calculated by standard procedure accroding to Dr. Waud, Analysis of dose-response curves, in "Methods in Pharmacology" vol. 3, Smooth muscle, Ed. Daniel, E. E. Paton, M., Plenum Press, New York (1975); Ash and Schild, Br. J.Pharmacol. Chemother. 27, 427–439, 1966. The following table shows the results obtained:

TABLE I

In vitro inhibitory activity of histamin-induced tachycardia (guinea pig atria)

| Compound of Example | $EC_{50}$ $10^{-7}$ M |
| --- | --- |
| 14 | 3.3 |
| 14(a) | 5.3 |
| 14(b) | 2.8 |
| 14(c) | 2.0 |
| 14(d) | 5.5 |
| 14(e) | 3.0 |

TABLE I-continued

In vitro inhibitory activity of histamin-induced tachycardia (guinea pig atria)

| Compound of Example | $EC_{50}$ $10^{-7}$ M |
| --- | --- |
| 14(f) | 12.0 |
| 14(j) | 3.3 |
| 14(l) | 31.0 |
| 14(p) | 4.8 |
| 14(s) | 2.7 |
| 14(ap) | 4.5 |
| CIMETIDINE | 34.0 |

The ability of the test compounds to inhibit histamine-induced gastric secretion of acid was investigated after intravenous or intraduodenal administration in stomach-perfused rats, according to Gosh and Schild, Br. J. Pharmacol. Chemother. 13, 54, (1958).

The preparation of the animals under general anesthesia (urethane, 1 g/kg i.p.) and constant temperature, was achieved by inserting and tying in place polyethyl tubes (PE 50) in the esophagus and in the pyloricantral region. After the stomach was washed to remove residual of foods, continuous perfusion of the stomach was started with saline, 0.5 ml/min. (37° C.), primed by a Jobling peristaltic pump. After 30 minutes of perfusion adaptation, the stomach perfusate was collected in 30 min. samples, and titrated for acid content, expressed as $\mu$Eq of NaOH 1N. As control acid output became constant, intravenous perfusion of histamine (1 mg/kg/hr) was started and maintained throughout the experimental period. After the acid secretion had reached the steadily higher level, increasing doses of the test compounds were injected intravenously in order to obtain dose-response functions. The $ED_{50}$ was then calculated by standard procedure.

The compounds tested by the afore-mentioned procedure showed a very potent antisecretory activity when administered intravenously at or below 100 $\mu$g/kg.

The results are shown in the following table:

TABLE II

In vivo antisecretory activity of histamin-induced gastric secretion (stomach-perfused rat).

| Compound of Example | $ED_{50}$ mg $\cdot$ kg$^{-1}$ (i.v.)* |
| --- | --- |
| 14 | 0.020 |
| 14(a) | 0.013 |
| 14(b) | 0.019 |
| 14(c) | 0.035 |
| 14(d) | 0.073 |
| 14(e) | 0.041 |
| 14(f) | 0.082 |
| 14(j) | 0.020 |
| 14(l) | 0.074 |
| 14(p) | 0.050 |
| 14(s) | 0.028 |
| 14(ap) | 0.051 |
| CIMETIDINE | 0.560 |

*The values of activity are expressed taking the compound as a base.

The acute toxicity of the particularly preferred compounds of the formula I was approximately determined by oral administration of a single dose to groups of 5 Swiss mice, fasted for 18 hours before the test. The evaluation of the incidence of mortality was considered 14 days after the administration. The results are shown in the following table, in which the values are expressed taking the compound as a base.

TABLE III

| Compound of Example | No. Dead/No. Treated Mice |
|---|---|
| 14 | 0/5 at 500 mg/kg |
| 14(a) | 0/5 at 500 mg/kg |
| 14(b) | 0/5 at 500 mg/kg |
| 14(c) | 1/5 at 500 mg/kg |
| 14(d) | 4/5 at 500 mg/kg |
| 14(e) | 0/5 at 500 mg/kg |
| 14(f) | 0/5 at 500 mg/kg |
| 14(j) | 0/5 at 500 mg/kg |
| 14(l) | 0/5 at 500 mg/kg |
| 14(p) | 0/5 at 500 mg/kg |
| 14(s) | 0/5 at 500 mg/kg |
| 14(ap) | 0/5 at 500 mg/kg |

For pharmaceutical purposes the compounds of the present invention are administered to warm-blooded animals perorally or parenterally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups and the like. An effective amount of the compounds according to the present invention is from 0.14 to 7.14 mgm/kg body weight, preferably 0.28 to 2.14 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 17

Tablets

The tablet composition is compounded from the following ingredients:

| | |
|---|---|
| N—Methyl-N'—[3-(2-guanidino-4-thiazolyl)-phenyl]-formamidine | 50 parts |
| Lactose | 217 parts |
| Corn starch | 30 parts |
| Magnesium stearate | 3 parts |
| Total | 300 parts |

Preparation:

The active ingredient, the lactose and the corn starch are combined, and the mixture is homogeneously moistened with water. After screening of the moist mass and drying in a tray dryer, the mixture is again passed through a screen, and the magnesium stearate is added. Then, the mixture is compressed into tablets weighing 300 mg each. Each tablet contains 50 mg of active ingredient.

EXAMPLE 18

Gelatin capsules

The capsule filler composition is compounded from the following ingredients:

| | |
|---|---|
| N—Ethyl-N'—[3-(2-guanidino-4-thiazolyl)-phenyl]-formamidine | 50 parts |
| Corn starch | 170 parts |
| Magnesium stearate | 2 parts |
| Total | 222 parts |

Preparation:

The active ingredient is mixed with the inert ingredients, and the mixture is passed through a screen and mixed homogeneously in a suitable device. The resulting mixture is filled into hard gelatin capsules (222 mg per capsule); each capsule contains 50 mg of the active ingredient.

EXAMPLE 19

Injection solution

The solution is compounded from the following ingredients:

| | |
|---|---|
| N—Propyl-N'—[3-(2-guanidino-4-thiazolyl)-phenyl-formamidine | 50 parts |
| Water for injection | q.s. ad 5000 parts by vol. |

Preparation:

The active ingredient is dissolved in the water, and the resulting solution is filled into 5 cc-ampules under sterile conditions. Each ampule contains 50 mg of the active ingredient.

Any one of the other compounds embraced by formula I or a non-toxic, pharmacologically acceptable acid addition salt thereof may be substituted for the particular active ingredient in Examples 17 through 19. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the tautomeric formula

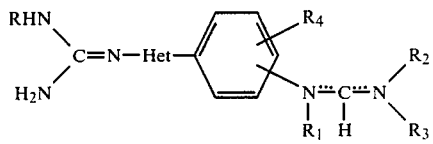

wherein

R, $R_1$ and $R_2$, which may be identical to or different from each other, are each hydrogen or alkyl of 1 to 4 carbon atoms;

$R_3$ is straight or branched lower alkyl, optionally interrupted by an oxygen, sulfur or nitrogen heteroatom; straight or branched lower alkenyl; lower alkynyl; cyano; cycloalkyl of 3 to 7 carbon atoms; (cycloalkyl of 3 to 7 carbon atoms) (alkyl of 1 to 4 carbon atoms); norbornyl; phenyl; or a 5- to 6-membered ring comprising carbon atoms and one to two nitrogen, oxygen or sulfur heteroatoms; or $R_2$ and $R_3$, together with each other and the nitrogen atom to which they are attached, are pyrrolidino, morpholino or piperidino;

$R_4$ is hydrogen, halogen, alkyl of 1 to 4 carbon atoms or alkoxy of 1 to 4 carbon atoms; and Het is a thiazole, oxazole, 1,2,4-thiadiazole, 1,3,4-thiadiazole or 1,2,4-oxadiazole ring;

a tautomer thereof, or a non-toxic, pharmacologically acceptable acid addition satlt thereof.

2. A non-toxic pharmacologically acid addition salt of a compound of claim 1.

3. An acid addition salt of claim 2, which is the hydrochloride, sulfate, maleate or fumarate.

4. A compound of claim 1, where the amidine radical is in the meta-position of the benzene ring with respect to the Het group.

5. A compound of the formula

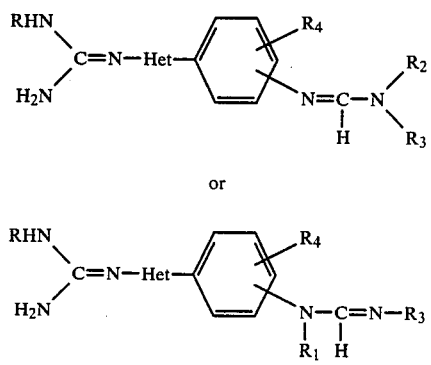

wherein R, $R_1$, $R_2$, $R_3$, $R_4$ and Het have the meanings defined in claim 1.

6. A compound of claim 5 of the formula

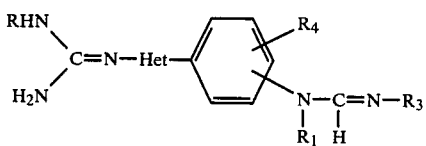

wherein R, $R_1$ and $R_4$ are hydrogen, $R_3$ is methyl, ethyl, n-propyl, isopropyl, n-butyl, isobutyl, sec.butyl, neopentyl, n-hexyl, n-octyl, allyl, dimethylallyl, propargyl, cyclopropylmethyl, cyclohexyl, norbornyl, phenyl, pyridyl, hydroxypropyl, methoxyethyl, methylthioethyl or cyanoethyl, and Het is thiazolyl or 1,2,4-thiadiazolyl, or a non-toxic, pharmacologically acceptable acid addition salt thereof.

7. A compound of claim 1, which is N-methyl-N'-[3-(2-guanidino-4-thiazolyl)-phenyl]-formamidine or a non-toxic, pharmacologically acceptable acid addition salt thereof.

8. A compound of claim 1, which is N-ethyl-N'-[3-(2-guanidino-4-thiazolyl)-phenyl]-formamidine or a non-toxic, pharmacologically acceptable acid addition salt thereof.

9. A compound of claim 1, which is N-propyl-N'-[3-(2-guanidino-4-thiazolyl)-phenyl]-formamidine or a non-toxic, pharmacologically acceptable acid addition salt thereof.

10. A compound of claim 1, which is N-isopropyl-N'-[3-(2-guanidino-4-thiazolyl)-phenyl]-formamidine or a non-toxic, pharmacologically acceptable acid addition salt thereof.

11. A compound of claim 1, which is N-butyl-N'-[3-(2-guanidino-4-thiazolyl)-phenyl]-formamidine or a non-toxic, pharmacologically acceptable acid addition salt thereof.

12. A compound of claim 1, which is N-sec.butyl-N'-[3-(2-guanidino-4-thiazolyl)-phenyl]-formamidine or a non-toxic, pharmacologically acceptable acid addition salt thereof.

13. A compound of claim 1, which is N-isobutyl-N'-[3-(2-guanidino-4-thiazolyl)-phenyl]-formamidine or a non-toxic, pharmacologically acceptable acid addition salt thereof.

14. A compound of claim 1, which is N-allyl-N'-[3-(2-guanidino-4-thiazolyl)-phenyl]-formamidine or a non-toxic, pharmacologically acceptable acid addition salt thereof.

15. A compound of claim 1, which is N-propargyl-N'-[3-(2-guanidino-4-thiazolyl)-phenyl]-formamidine or a non-toxic, pharmacologically acceptable acid addition salt thereof.

16. A compound of claim 1, which is N-(2-methoxyethyl)-N'-[3-(2-guanidino-4-thiazolyl)-phenyl]-formamidine or a non-toxic, pharmacologically acceptable acid addition salt thereof.

17. A compound of claim 1, which is N-(3-hydroxypropyl)-N'-[3-(2-guanidino-4-thiazolyl)-phenyl]-formamidine or a non-toxic, pharmacologically acceptable acid addition salt thereof.

18. A compound of claim 1, which is N-ethyl-N'-[3-(5-guanidino-1,2,4-thiadiazol-3-yl)-phenyl]-formamidine or a non-toxic, pharmacologically acceptable acid addition salt thereof.

19. An anti-ulcerogenic pharmaceutical composition consisting essentially of an inert pharmaceutical carrier and an effective anti-ulcerogenic amount of a compound of claim 1.

20. The method of inhibiting the formation of gastric ulcers in a wam-blooded animal in need thereof, which comprises perorally or parenterally administering to said animal an effective anti-ulcerogenic amount of a compound of claim 1.

* * * * *

UNITED STATES PATENT AND TRADEMARK OFFICE
CERTIFICATE OF CORRECTION

PATENT NO. : 4,548,944                      Page 1 of 2

DATED : Oct. 22, 1985

INVENTOR(S) : GIUSEPPE BIETTI ET AL.

It is certified that error appears in the above-identified patent and that said Letters Patent is hereby corrected as shown below:

Column 1, line 65:   Should be a new paragraph

Column 2, line 43:   "the" should read -- an --.

Column 2, line 58:   "carbom" should read -- carbon --.

Column 4, line 62:   "of" should read -- or --.

Column 6, line 58:   "[5-chloro" should read -- [6-chloro --.

Column 7, line 5:   "N-Cyano" should read -- (p) N-Cyano --.

Column 8, line 15:   "(4amino" should read -- (4-amino --.

Column 8, line 19:   "5Guanidino" should read -- 5-Guanidino --.

Column 8, line 39:   "then" should read -- the --.

Column 10, line 21:   "Cal." should read -- Calc. --.

Column 10, line 49:   "quanidino" should read -- guanidino --.

Column 13, line 45:   "4morpholinyl" should read -- 4-morpholinyl --.

Column 13, line 66:   "5methyl" should read -- 5-methyl --.

Column 15, line 25:   "(2quanidino" should read -- (2-guanidino --.

UNITED STATES PATENT AND TRADEMARK OFFICE
CERTIFICATE OF CORRECTION

PATENT NO. : 4,548,944

DATED : Oct. 22, 1985

INVENTOR(S) : GIUSEPPE BIETTI ET AL.

Page 2 of 2

It is certified that error appears in the above-identified patent and that said Letters Patent is hereby corrected as shown below:

Column 15, line 41: "(2-quanidino" should read -- (2-guanidino --.

Column 15, line 49: "(2quanidino" should read -- (2-guanidino --.

Column 15, line 57: "(2-quanidino" should read -- (2-guanidino --.

Column 16, line 59: "diethyl precipitated" should read -- diethyl ether precipitated --.

Column 17, line 16: "[3-guanidino" should read -- [3-(2-guanidino --.

Column 21, line 2: "satlt" should read -- salt --.

Signed and Sealed this

Fourth Day of February 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,548,944
DATED : Oct. 22, 1985
INVENTOR(S) : GIUSEPPE BIETTI ET AL.

It is certified that error appears in the above-identified patent and that said Letters Patent is hereby corrected as shown below:

Column 17, line 48: "chronotropic obtained" should read
-- chronotropic response obtained --.

Column 22, line 48: "wam-blooded" should read
-- warm-blooded --.

Signed and Sealed this

Eighteenth Day of March 1986

[SEAL]

Attest:

DONALD J. QUIGG

Attesting Officer

Commissioner of Patents and Trademarks